United States Patent [19]

Delevallee et al.

[11] Patent Number: 4,879,298

[45] Date of Patent: Nov. 7, 1989

[54] NOVEL METHOD AND COMPOSITION

[75] Inventors: Francoise Delevallee, Fontenay Sous Bois; Pierre Potier, Paris, both of France

[73] Assignee: Roussel Uclaf, Paris, France

[21] Appl. No.: 180,380

[22] Filed: Apr. 12, 1988

[30] Foreign Application Priority Data

Apr. 15, 1987 [FR] France .................................. 87 05362

[51] Int. Cl.⁴ ............................................. A61K 31/44
[52] U.S. Cl. .................................................... 514/282
[58] Field of Search ......................................... 514/282

[56] References Cited

PUBLICATIONS

Chem. Abst. 104-200655v (1986)t, 106-78647t (1987).

Primary Examiner—Stanely J. Friedman
Attorney, Agent, or Firm—Bierman & Muserlian

[57] ABSTRACT

A novel method of relieving pain in warm-blooded animals, including humans, comprising administering to warm-blooded animals an analgesically effective amount of a central analgesic and forskoline simultaneously, separately or at different times and novel analgesic compositions.

6 Claims, No Drawings

NOVEL METHOD AND COMPOSITION

STATE OF THE ART

Forskoline is a derivative of labdanum type, the structure of which is given, for example, in German Pat. No. 2,557,784. Numerous pharmacological properties have been described for this product such as anti-hypertensive, platelet anti-aggregating, bronchodilating, and cyclase adenylate stimulating properties ("Drugs of the future", Vol 4 p. 26 (1979) and Vol 7 (1) p. 55 (1982) and anti-inflammatory and oxygenating properties, (German Pat. No. 3,502,686-A). Other references can be cited as European Application EP.A 0192056 and PCT Application W.O.A. 8502616 as well as U.S. Pat. Nos. 4,088,659 and 4,118,508.

Furthermore, the central analgesics or narcotics are generally considered as possessing the same characteristics as morphine, that is, they cause toxicomania and bring on respiratory depression. The synthetic derivatives of morphine most used in therapeutics are pethidine, dextromoramide and pentazocine and these derivatives present the same inconveniences as morphine and research for derivatives possessing the same powerful analgesic effect as morphine and deprived of toxicomanogenic action has remained fruitless up to the present.

OBJECTS OF THE INVENTION

It is an object of the invention to provide novel analgesic compositions and a novel method of relieving pain in warm-blooded animals.

These and other objects and advantages of the invention will become obvious from the following detailed description.

THE INVENTION

The novel method of the invention for relieving pain in warm-blooded animals comprises administering to warm-blooded animals an analgesically effective amount of a central analgesic and forskoline simultaneously, separately or at different times.

The combination of forskoline with a central analgesic gives a greater analgesic effect than with the central analgesic alone. Experiments on animals have shown potentiation of the effect of the central analgesic with an inactive dose of forskoline.

This means that the method of the invention gives an important analgesic action with a lower amount of central analgesic than that which would have been necessary to obtain the same level of activity and therefore, diminishes the secondary effects of the central analgesic used. This means that one can obtain the desired analgesic activity of the central analgesics while having reduced undesirable side effects.

Examples of the central analgesics useful in the present invention are morphine, pethidine, fentanyl, pentazocine or dextromoramide. However, the preferred central analgesic is morphine.

Typical of the undesired side effects of central analgesics derived from morphine at their normal doses are (1) nausea and vomiting, (2) constipation, (3) respiratory depression, (4) physical and/or mental habituation during prolonged treatment and (5) withdrawal symptoms at the end of the treatment including mydriasis, muscular contractions, headaches, sweating, vomiting, diarrhea, tachycardia, panting, hyperthermia and hypertension.

The effect of the claimed method is particularly useful for lessening the physical and mental dependence as well as the habituation which develops after repeated administration of morphine-type analgesics. Therefore, the combination of forskoline and a morphine analgesic is deemed to be "an economizer for morphine." The combination permits the dose of morphine, for example, to be reduced by about 2 to 5 times.

The pharmaceutical compositions of the invention are comprised of an analgesically effective amount of a mixture of central analgesic and forskoline and an excipient. The compositions may be in the form of tablets, dragees, gelules, capsules, granules, suppositories and injectable solutions or suspensions.

Examples of the excipients are talc, gum arabic, lactose, starch, magnesium stearate, aqueous or non-aqueous vehicles, fatty substances of animal or vegetable origin, paraffin derivatives, glycols, various wetting, dispersing and emulsifying agents and preservatives.

The compositions are useful in the treatment of severe pains in particular, those resistant to peripheral antalgesics for example, for neoplasia, in the treatment of pancreatitis, renal or biliary colic, in the treatment of post-operation and post-traumatic pains.

The relative proportions of the central analgesic and forskoline in the compositions of the invention can vary. The proportions depend greatly on the analgesic activity of the central analgesic used, depending upon whether the analgesic chosen is morphine or an analgesic which is more active than morphine such as pethidine, fentanyl or dextromoramide or less active than morphine such as pentazocine. The proportions can vary. They can be 1 part of forskoline per 0.01 to 20 parts by weight of the central analgesic and preferably, 1 part of forskoline per 0.1 to 20 parts by weight of the central analgesic.

The novel method of the invention for relieving pain in warm-blooded animals comprises administering to warm-blooded animals an analgesically effective amount of a central analgesic and forskoline in succession or together or at intervals ranging from several seconds to 1 or several hours up to 15 hours apart. The compositions may be administered orally or parenterally. When they are administered parentally, they are preferably administered simultaneously. The two constituents of the combination can be administered by various administration routes and thus, can be presented in the form of a kit with two components containing on the one hand forskoline in a pharmaceutical form intended for oral administration and the central analgesic on the other hand in a pharmaceutical form for parenteral administration.

The dosage will vary as a function of the condition being treated and the administration route as well as the patient in question. For example, one may administer 1 part by weight of the central analgesic and 5 to 20 parts by weight of forskoline orally and 0.2 to 5 parts by weight of forskoline subcutaneously.

In the following examples, there are described several preferred embodiments to illustrate the invention. However, it is to be understood that the invention is not intended to be limited to the specific embodiments.

EXAMPLE 1

An injectable solution was prepared by combining 5 mg of morphine hydrochloride, 10 mg of forskoline and sufficient sterile solvent for a final solution of 2 ml.

An injectable solution was also prepared by combining 2 ml of an injectable solution of 0.25% morphine hydrochloride and 5 mg of forskoline. The said solution could be prepared just before use by adding the forskoline to the injectable solution and stirring the mixture.

An example of a pharmaceutical kit comprises a tablet of 50 mg of forskoline and sufficient excipient of lactose, starch, magnesium stearate and talc to obtain a final tablet weight of 350 mg. The second component of the kit would be 2 ml of an injectable solution of 0.25% morphine hydrochloride.

PHARMACOLOGICAL DATA

The test used was the potentiation of the analgesic activity of morphine on a hot plate test with mice. Female mice weighing 20 to 22 g were placed individually on a copper plate maintained at 56° C. and reaction to the pain was shown by the animal licking one or both of its front paws. The time of this reaction was noted and only those mice reacting in less than 10 seconds were retained for the test. The mice were distributed into homogeneous groups with one group receiving only the vehicle of the products being administered. Forskoline was administered at a dose inactive by itself of 5 mg/kg subcutaneously or at a dose of 50 mg/kg orally simultaneously with an injection of morphine hydrochloride in the first case, and 5½ hours before the injection of morphine hydrochloride in the second case. The reaction time of the mice to the pain was noted 30 minutes after the treatment. The increase in the reaction time after 30 minutes after the administration of morphine is indicated in the following table:

| | | |
|---|---|---|
| Morphine | 3 mg/kg s.c. | 102% |
| Forskoline | 5 mg/kg s.c. + | } 209% |
| Morphine | 3 mg/kg s.c. | |
| Morphine | 3 mg/kg s.c. | 86% |
| Forskoline | 50 mg/kg o.r. + | } 170% |
| Morphine | 3 mg/kg o.r. | |

It can easily be seen from the results of the table that the combination increased the analgesic activity of the morphine by at least 100%.

Various modifications of the compositions and method of the invention may be made without departing from the spirit or scope thereof and it should be understood that the invention is intended to be limited only as defined in the appended claims.

What is claimed is:

1. A method of relieving pain in warm-blooded animals comprising administering to warm-blooded animals an analgesically effective amount of a central analgesic which is less than that normally used and sufficient forskoline to potentialize the central analgesic simultaneously or successively at times from a few seconds up to 15 hours, the central analgesic; forskoline ratio being 1 part by weight to 0.01 to 20 parts by weight.

2. The method of claim 1 wherein the central analgesic is selected from the group consisting of morphine, pethidine, fentanyl, pentazocine or dextromoramide.

3. The method of claim 1 wherein the central analgesic is morphine.

4. The method of claim 1 wherein the weight ratio of forskoline to central analgesic is 1 to 0.1 to 20.

5. The method of claim 1 wherein the central analgesic and forskoline are administered simultaneously.

6. The method of claim 1 wherein the central analgesic and forskoline are administered together.

* * * * *